US00PP08423P

United States Patent [19]

Douglass

[11] Patent Number: Plant 8,423

[45] Date of Patent: Oct. 19, 1993

[54] BLACKBERRY-DOUGLASS CULTIVAR

[76] Inventor: Bernard S. Douglass, 27825 NW. Truitt Rd., Hillsboro, Oreg. 97124

[21] Appl. No.: 775,019

[22] Filed: Oct. 11, 1991

[51] Int. Cl.[5] ..... A01H 5/00
[52] U.S. Cl. ..... Plt./46.1
[58] Field of Search ..... Plt. 46.1

*Primary Examiner*—James R. Feyrer
*Assistant Examiner*—E. F. McElwain
*Attorney, Agent, or Firm*—Chernoff, Vilhauer, McClung & Stenzel

[57] ABSTRACT

A new and distinct variety of trailing type blackberry plant characterized by husky, thornless canes and a vigorous growth habit. The variety has a high mid-season fruit yield of medium large glossy black fruit with excellent dessert and canning qualities.

2 Drawing Sheets

SUMMARY OF INVENTION

The new and distinst variety of thornless blackberry described herein originated from a hand-pollinated cross of two non-patented parents, Sander and Lawrence, which were also created by the applicant at his resident blackberry breeding facilities near Hillsboro, Oreg.

The seeds resulting from this controlled hybridization were germinated in the applicant's greenhouse in the spring of 1985 and planted in an outdoor experimental plot in the early summer of 1985. The seedlings first lightly bore fruit during the summer of 1986. The subject cultivar was selected for its thornless cane, vigorous trailing vines, high berry productivity, and large, firm, black fruit of high quality. A pedigree of the claimed cultivar is summarized in FIG. 3.

During 1987, the above described cultivar was propagated asexually both by cane layering and cane cuttings for the purpose of further testing and evaluations by research horticulturists at Oregon State University's Department of Horticulture. The researchers found the cultivar to have outstanding potential.

In 1989 Oregon State University's North Willamette Agricultural Experiment Station at Aurora, Oreg., included samples of the cultivar in their blackberry test plots. Test at other locations show that the cultivar may adapt to other areas of the Pacific Northwest outside of Northwestern Oregon.

During all asexual multiplication, the characteristics of the original plant have been maintained and no aberrant phenotypes have appeared.

Plants of the cultivar are highly vigorous and develop large diameter canes. Although nominally thornless, the lower 12- to 18-inch bases of the canes do contain small, soft incipient type spines similar to those found on raspberry canes. These small spines tend to disappear completely from the canes at a point about 12 to 18 inches above the ground level. The plants are genetically thornless, having genes for thornlessness derived from its distant "Austin Thornless" ancestor. Plants are moderately resistant to blackberry leaf and cane spot (Septoria rubi) which is a major cause of blighted foliage on a number of other Northwest adapted blackberry cultivars.

Fruit of the new cultivar ripens in mid-July about the same time as "Marion," a leading Northwest standard cultivar. The harvest period is about 20 days duration.

The plants have never suffered from spring frosts and the canes have survived winter temperatures of 5° F.

The fruit varies in shape from bluntly cone shaped to bluntly pointed cylindrical. The length of the fruit usually exceeds its diameter by about 40%.

Fruit clusters are medium large and borne on long stout stems which facilitate easy picking. Flower fertility is high and fruit druplets tend to fill out the berries completely.

BRIEF DESCRIPTION OF THE DRAWINGS

The accompanying color photographs (FIGS. 1 and 2) show typical blossoms, foliage, and fruit of the cultivar. A pencil is shown in the fruit picture to help delineate the berry size.

DETAILED DESCRIPTION OF THE NEW VARIETY

Figure 1:
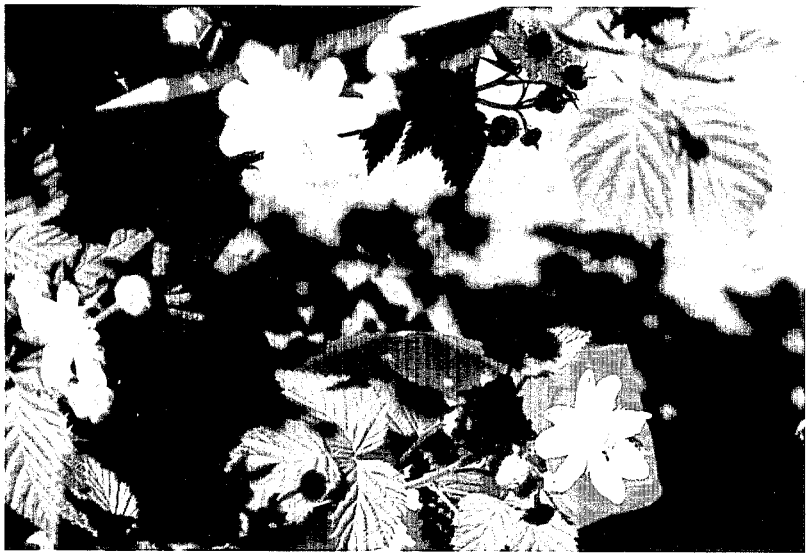
Figure 2:
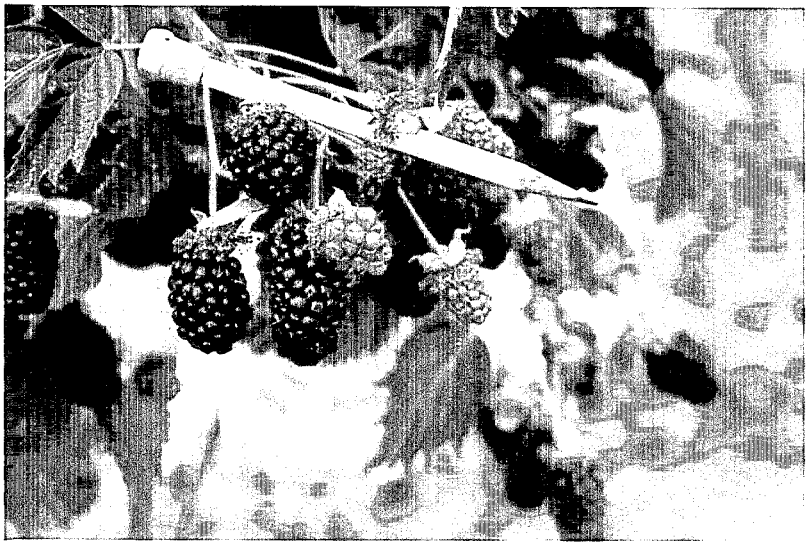
Figure 3:
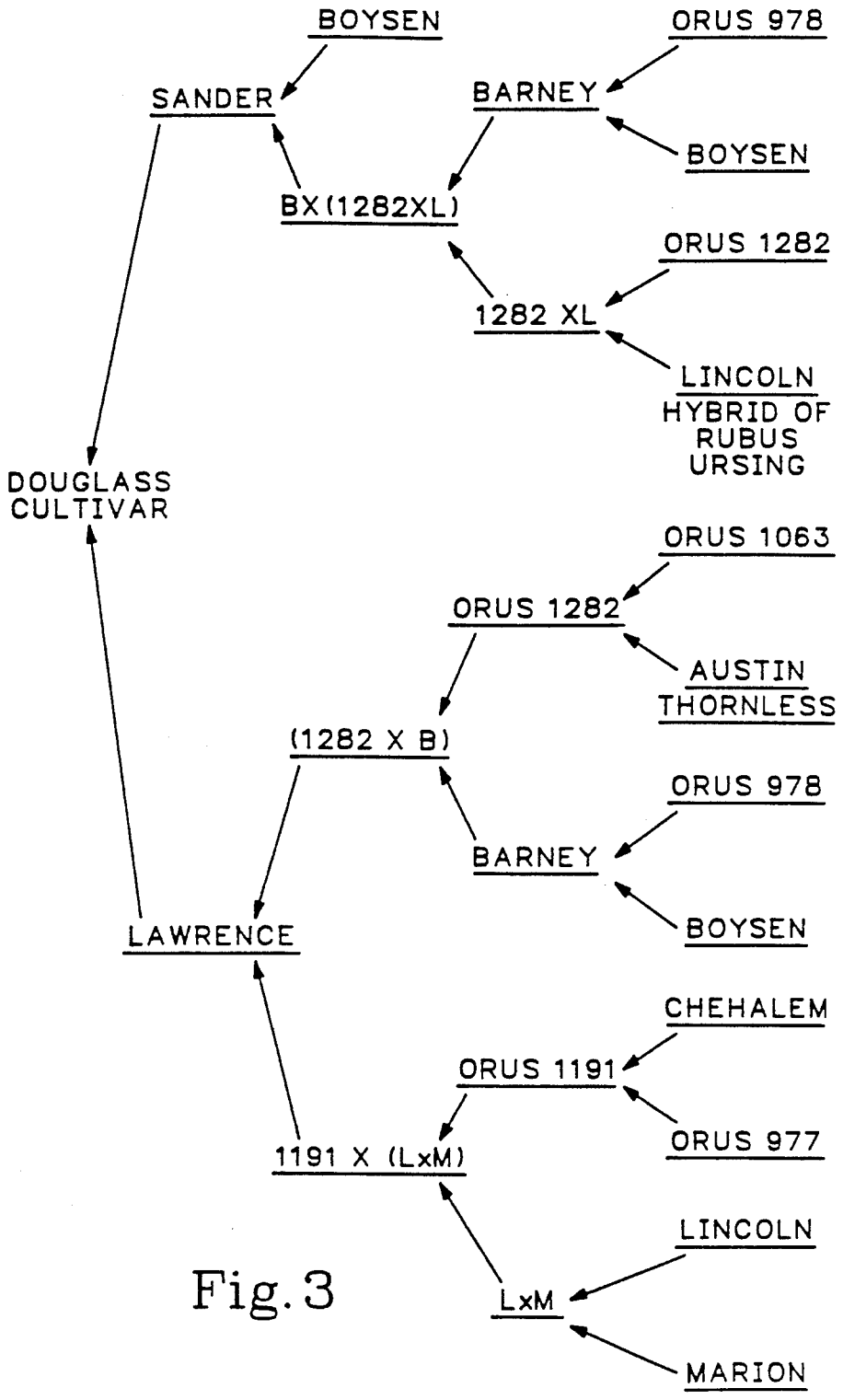
FIG. 3 shows the pedigree of the claimed cultivar.

The following is a detailed description of the pomological characteristics of the subject blackberry cultivar. Color terminology is in accordance with that of The Royal Horticulture Society Colour Chart published in 1966 by The Royal Horticulture Society of London, England.

Where dimensions, sizes, colors, and other characteristics are given, it is to be understood that such characteristics are approximations of averages set forth as accurately as practicable.

The described plants, canes (primocane equals one-year and floricane equals two-year fruiting cane) and fruits are specimens grown at the Douglass home farm near Hillsboro, Oreg.

Plant:

*Size (Primocanes).*—Large, trailing, type; 3–4 m in length, occasionally 5 m.

*Growth.*—Very vigorous with prolific crown cane production from 6–10 canes per crowns.

*Productivity.*—High over a period of 20 days. Consistent bearer from year to year.

*Cold hardiness.*—Medium high, about the same as Marion.

*Canes (Floricanes and Primocanes).*—Trailing type and thornless except for small raspberry-like spines near the base of the canes. Internodal spans average 6.5 cm. at base and 7.6 cm. at the midpoint of the canes. Cane diameters average 1.4 cm. at the base and 1.0 cm. at the midpoint.

*Cane color.*—Primocane: Immature cane color Yellow/Green Group (146C). Floricane: Mature cane color: Grayed-Purple Group (187B).

Foliage:

*Color.*—Green group (137B); occasional reddish tinges as they age.

*Primocane compound leaf.*—Large with usually 5, and sometimes 7, leaflets per compound leaf; more triangular in shape and deeper, sharper serrations than standard trailing cultivar Marion. Terminals: 8-12 cm long, 6-8 wide.

*Mid cane.*—14-18 cm long, 15-17 cm wide.

*Floricane compound on fruiting laterals.*—14-16 cm long, 15-17 cm wide.

Flower:

*Date of first bloom.*—May 10 average.

*Date of last bloom.*—May 30 average.

*Blossom color.*—White.

*Reproduction organs.*—Perfect flowers with abundant pollen and numerous pistils and stamens.

*Petals per flower.*—Usually 8, but occasional double blossoms are produced with up to 16 petals.

*Anthers.*—Anther retention during fruit ripening exceeds anther retention for other known trailing type blackberries.

*Average number of flowers per cluster.*—7.

Fruit:

*Maturity.*—Mid-season with average period of maturity from about July 5 to July 25; 4-5 weekly harvests; 5.1 average; range 4.1-6.1 g over a 4-week harvest seasons.

*Size.*—Medium large, slightly larger than Marion.

*Productivity.*—Compares with Marion, a thorny selection and standard West Coast trailing cultivar. Fruit diameter averages about 2.0 cm. and fruit length about 2.8 cm.

*Shape.*—Bluntly conical to bluntly pointed cylindrical.

*Color.*—Glossy black.

*Skin.*—Medium tenderness.

*Druplet size.*—Medium large with small seeds.

*Firmness.*—Medium firm, about the same as standard cultivar, Marion. Pressure test 600-1000 g of force compared with 550-1000 g for Marion.

*Ease of harvest.*—Easy; suitable for machine harvest; equal to standard cultivar Marion.

*Flavor.*—Excellent blackberry taste. Sweet with pleasing medium acid tang.

*PH.*—3.53 (compared with 3.19 for Marion). Soluble solids: 13.2% (compared with 12.8% for Marion). Titract acids: 1.560& (compared with 1.391% for Marion). Number of seeds per 5 g of berry puree: 47 (compared with 50 for Marion). Individual seet wt.: 1.91 mg (compared with 2.53 mg. for standard cultivar Marion). Seed wt. as % of berry wt.: 1.8% (compared with 2.5% for standard cultivar Marion).

*Uses.*—Fresh and processed for jellies, jams, and juice.

*Traning and pruning requirements.*—Normally handled the same as standard trailing blackberries such as Marion, Logan, Boysen, etc., which require a two-wire trellis of approximately 1.5 m in height. Annually, the floricanes are removed and the primocanes are placed on the trellis wire, usually during late summer or early spring.

What is claimed is:

1. A new and distinct trailing type blackberry as substantially illustrated and described which is characterized by husky, thornless canes and a vigorous growth habit, and high mid-season fruit yields of medium large glossy black fruit with small seeds, excellent dessert qualities and high potential for jams, jellies, and juice.

* * * * *